US00PP28762P2

(12) United States Plant Patent
Ault

(10) Patent No.: US PP28,762 P2
(45) Date of Patent: Dec. 12, 2017

(54) ***PHLOX* PLANT NAMED 'STRAWBERRIES AND CREAM'**

(50) Latin Name: ***Phlox* hybrid**
Varietal Denomination: Strawberries and Cream

(71) Applicant: James Robert Ault, Libertyville, IL (US)

(72) Inventor: James Robert Ault, Libertyville, IL (US)

(73) Assignee: CHICAGO LAND GROWS, INC., Glencoe, IL (US)

( * ) Notice: Subject to any disclaimer, the term of this patent is extended or adjusted under 35 U.S.C. 154(b) by 0 days.

(21) Appl. No.: 15/330,021

(22) Filed: Jul. 26, 2016

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Annette Para
(74) *Attorney, Agent, or Firm* — Penny J. Aguirre

(57) ABSTRACT

A new cultivar of *Phlox* plant named, 'Strawberries and Cream', that is characterized by its low dense groundcover habit, its flowers that emerge white in color lightly suffused with violet pink ageing to a medium and then dark pink-violet color, its petals that overlap for one-quarter to one-half of their length, its petal striae that are purple in color becoming masked by a ring of dark purple pigment that accumulates in the corolla tube throat as the flowers age, and its flowers that cover 90% or more of the plant at peak bloom.

2 Drawing Sheets

Botanical classification: *Phlox* hybrid.
Cultivar designation: 'Strawberries and Cream'.

BACKGROUND OF THE INVENTION

The present invention relates to a new and distinct cultivar of *Phlox* plant, botanically an interspecific hybrid known as *Phlox* 'Strawberries and Cream' and will be referred to hereafter by its cultivar name, 'Strawberries and Cream'. The new cultivar represents a new moss *phlox*, a herbaceous perennial grown for landscape use.

The new invention arose from an ongoing controlled breeding program conducted by the Inventor in Glencoe, Ill. The objectives of the breeding program are to develop improved cultivars of interspecific *Phlox* hybrids with novel ornamental traits such as unique flower colors, plant habits, flower fragrance and adaptability to garden conditions in the upper Midwest (U.S.D.A. Zone 5) and similar climates.

'Strawberries and Cream' was derived from a cross made in April of 2010 under controlled conditions between *Phlox subulata* 'Scarlet Flame' (not patented) as the female parent and *Phlox kelseyi* 'Lemhi Midnight' (not patented) as the male parent. The resulting seedlings were planted for evaluation in June of 2011. 'Strawberries and Cream' was selected in May of 2012 as a single unique plant amongst the resulting seedlings.

Asexual propagation of the new cultivar was first accomplished by shoot tip cuttings by the Inventor in June of 2013 in Glencoe, Ill. Asexual propagation by shoot tip cuttings has determined that the characteristics of this cultivar are stable and reproduced true to type in successive generations

SUMMARY OF THE INVENTION

The following traits have been repeatedly observed and represent the characteristics of the new cultivar. These attributes in combination distinguish 'Strawberries and Cream' as a unique cultivar of *Phlox*.

1. 'Strawberries and Cream' exhibits a low dense groundcover habit that is shorter in height than for most *Phlox*.
2. 'Strawberries and Cream' exhibits flowers that emerge white in color lightly suffused with violet pink, ageing to a medium and then dark pink-violet color.
3. 'Strawberries and Cream' exhibits petals that overlap for one-quarter to one-half of their length.
4. 'Strawberries and Cream' exhibits petal striae that are purple in color becoming masked by a ring of dark purple pigment that accumulates in the corolla tube throat as the flowers age.
5. 'Strawberries and Cream' exhibits flowers that cover 90% or more of the plant at peak bloom.

The female parent of 'Strawberries and Cream', 'Scarlet Flame', differs from 'Strawberries and Cream' in having flowers that are persistently medium to dark scarlet pink in color, in having a shorter bloom period that last for three to four weeks, in having smaller petals that only slightly overlap at the base, and in having larger more conspicuous petal striae. The male parent of 'Strawberries and Cream', 'Lemhi Midnight', differs from 'Strawberries and Cream' in having petals that lack striae, in having flowers with a distinct central eye, in having 50% or less flower coverage at peak bloom, and in having flowers that are persistently medium to deep blue-violet in color. 'Strawberries and Cream' can be most closely compared to the *Phlox subulata* cultivar 'Laura' (not patented) and the *Phlox kelseyi* cultivar 'Lemhi Purple' (not patented). 'Laura' is similar to 'Strawberries and Cream' in flower color at anthesis and in having 90% or more flower coverage at peak bloom. 'Laura' differs from 'Strawberries and Cream' in having flowers that remain light violet pink for the life of the flower, in having flowers that are smaller in size, in having flower petals that do not overlap, and in having petal striae that remain distinct for the life of the flower. 'Lemhi Purple' is similar to 'Strawberries and Cream' in having flowers of a similar size and in having a low spreading mat-forming plant habit that is short for a *Phlox* moss. 'Lemhi Purple' differs from 'Strawberries and Cream' in having flowers that lack striae, in having flowers with a central eye, in having narrow petals that do not overlap, and in having flowers that cover 50% or less of the plant at peak bloom.

BRIEF DESCRIPTION OF THE DRAWINGS

The accompanying colored photographs illustrate the overall appearance and distinct characteristics of the new *Phlox*. The photographs were taken of three year-old plants of 'Strawberries and Cream' as grown outdoors in a trail garden in Glencoe, Ill.

The photograph in FIG. 1 provides a top view of plants of 'Strawberries and Cream' in bloom and illustrates the low dense plant habit and 90% flower coverage.

Figure 1:
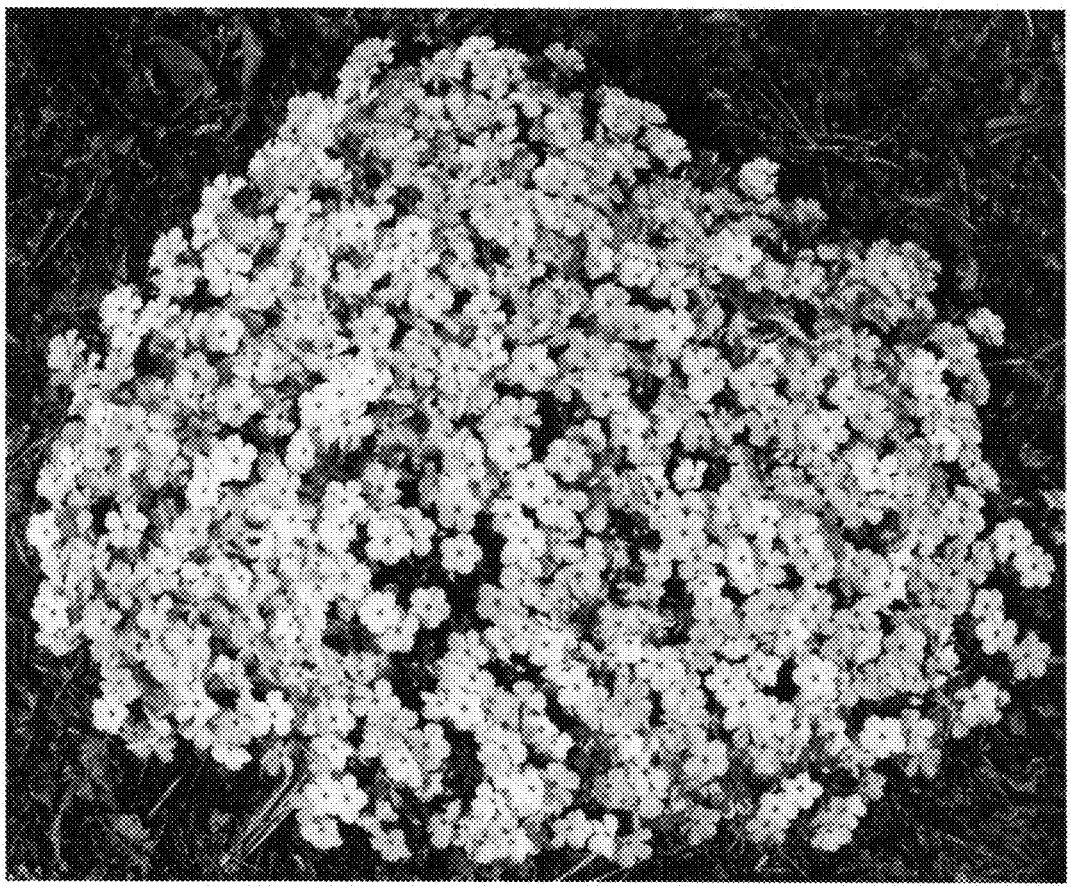
Figure 2:
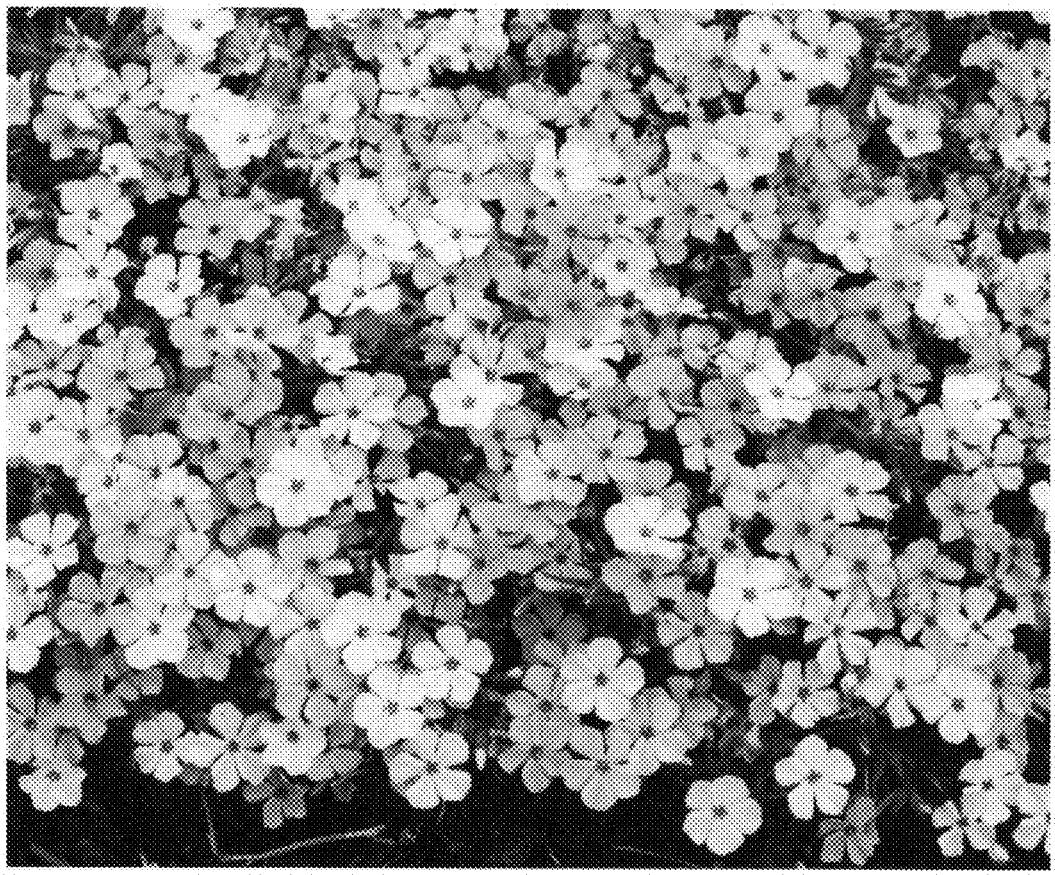

The photograph in FIG. 2 provides a close-up view of the flowers of 'Strawberries and Cream'.

The colors in the photographs are as close as possible with the photographic and printing technology utilized and the color values cited in the Detailed Botanical Description accurately describe the colors of the new *Phlox*.

DETAILED BOTANICAL DESCRIPTION OF THE PLANT

The following is a detailed description of three year-old plants of the new cultivar as grown outdoors in a trial garden in Glencoe, Ill. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Blooms for four to five weeks from late April to late May in northern Illinois.

*Plant type*.—Herbaceous perennial.

*Plant habit*.—Spreading, clump forming.

*Height and spread*.—An average of 10 cm in height and 38 cm in width.

*Hardiness*.—At least hardy in U.S.D.A. Zones 4 to 8.

*Diseases and pests*.—Resistance to powdery mildew (caused by *Erysiphe cichoracearum*) has been observed.

*Root description*.—Fibrous and NN155C in color.

*Growth rate*.—Moderate.

*Propagation*.—Shoot tip cuttings.

*Root development*.—Shoot tip cuttings will root under mist in four to six weeks in late spring to early summer, rooted cuttings will fully fill a 2.5 inch pot with roots in about three months and when transplanted in fall and overwintered in a 4-inch pot, they will bloom the following spring.

Stem description:

*Stem size*.—An average of 9 cm in length and 3 mm in width.

*Stem shape*.—Rounded.

*Stem strength*.—Moderately strong and flexible.

*Stem color*.—Young stems; 157A, flushed with 184A, mature stems; 161A.

*Stem surface*.—Young stems; smooth, very slightly glossy, and densely covered with wooly hairs about 1 mm in length, matching surface color, mature stems; slightly glossy and dry and paper like.

*Stem aspect*.—Held horizontally to descending, drooping and falling downward.

*Internode length*.—An average of 2 mm.

*Branching habit*.—Well branched, an average of 4 main stems growing from base of plant 9 cm in length.

Foliage description:

*Leaf shape*.—Lanceolate to linear.

*Leaf division*.—Simple.

*Leaf base*.—Truncate to cuneate.

*Leaf apex*.—Acute.

*Leaf venation*.—Pinnate, inconspicuous, matches leaf color on upper and lower surfaces.

*Leaf margins*.—Entire.

*Leaf attachment*.—Sessile.

*Leaf arrangement*.—Opposite and basal rosettes.

*Leaf surface*.—Smooth, shiny, margins sparsely covered with fine hairs an average of 1 mm in length and match leaf color.

*Leaf color*.—Upper and lower surface; 138A, base 138C.

*Leaf size*.—An average of 1 cm in length and 2 mm in width.

*Leaf quantity*.—An average of 19 basal rosettes per main stem, an average of 139 leaves per main stem, an average of 17 per lateral stem, on a stem 20 cm in length.

*Leaf fragrance*.—Fresh grass-like scent.

Flower description:

*Inflorescence type*.—Few-flowered cymes on terminus of lateral branches.

*Lastingness of inflorescence*.—About 3 to 4 weeks from the opening of the first flower to senescence of last flower, individual flower lasts about 5 days.

*Inflorescence size*.—An average of 6 cm in height and 4.7 cm in diameter.

*Flower fragrance*.—Slight pleasant fragrance.

*Flower number*.—An average of 6 per inflorescence.

*Flower aspect*.—Upright and outward from stem, upright from pedicel.

*Flower bud*.—Spatulate in shape with acute apex, an average of 1.6 cm in length and 3 mm in width, color; petal portion a blend of NN155D with hues of 62A and 62B and calyx portion; 137C with striations 138D.

*Flower form*.—Salverform.

*Flower size*.—An average of 1.6 cm in height and 2.1 cm in diameter.

*Corolla tube*.—An average of 1 cm in length and 2.5 mm in width (apex), outside surface color a blend of 182C and 144D, inside surface color 93A, glabrous and satiny surface on both surfaces.

*Corolla lobes*.—5, obcordate in shape, held nearly horizontally when fully open, slightly overlapping near base, slightly wavy in aspect, an average of 1 cm in length and 8 mm in width, apex rounded to broadly acute, base broadly cuneate and fused to tube, entire margins, color upper surface when opening; a blend of 65A, 65B, and 65C and blending into eye N155A and a pair of oblong striae N88B near base, color lower surface when opening; a blend of 65A, 65B, 65C and 65D with N155A at base, upper when fully open; a blend of 75C, 65B, 65C, and N155A with a pair of oblong striae N88B near base, lower surface when fully open; a blend of 75C, 65B, 65C, and N155A, glabrous and slightly satiny on upper and lower surfaces.

*Calyx*.—Campanulate in form, comprised of fused sepals with linear shaped sepal tips free, an average of 9 mm in length and 6 mm in width.

*Sepals*.—5, primarily fused with free tips, linear in shape, entire margins, fused base (about 75%), aristulate apex, an average of 9 mm in length and 1.5 mm in width, inner surface; glabrous, smooth, and shiny, outer surface; moderately covered with wooly hairs about 0.7 mm in length, inner and outer surface color 137C.

*Peduncles*.—Rounded in shape, an average of 1.2 cm in length and 1.5 mm in width, held upright to outward, color 182B, surface satiny and densely covered with wooly hairs about 0.5 mm in length, moderate in strength.

*Pedicels*.—Rounded in shape, an average of 2.5 cm in length and 1.5 mm in width, held at an average angle of 15° to peduncle, color 182B, surface satiny and densely covered with wooly hairs about 0.5 mm in length, moderate in strength.

Reproductive organs:

*Gynoecium*.—1 pistil, stigma; tri-lobed, each lobe is about 1 mm in length and 144D in color, style; about 8 mm in length and 0.3 mm in width, 144D in color, ovary; superior, ovate to oval in shape, about 1 mm in length and width, 143A in color.

*Androcoecium*.—5 stamens, anthers; dorsifixed, oblong in shape, 1.3 mm in length, and 23A in color, filaments; adnate to petals, an average of 5 mm in length and 155C in color, pollen is abundant in quantity and 23A in color.

*Seeds*.—None observed.

It is claimed:

1. A new and distinct cultivar of *Phlox* plant named 'Strawberries and Cream' as herein illustrated and described.

* * * * *